US008617586B2

(12) United States Patent
Nazarova et al.

(10) Patent No.: US 8,617,586 B2
(45) Date of Patent: Dec. 31, 2013

(54) HYDROPHILIC COATING THAT REDUCES PARTICLE DEVELOPMENT ON ESTER-LINKED POLY(ESTER-BLOCK-AMIDE)

(75) Inventors: Irina Nazarova, Woodbury, MN (US); Jeffrey S. Lindquist, Maple Grove, MN (US); Daniel J. Horn, Shoreview, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 528 days.

(21) Appl. No.: 12/704,390

(22) Filed: Feb. 11, 2010

(65) Prior Publication Data

US 2010/0217186 A1    Aug. 26, 2010

Related U.S. Application Data

(60) Provisional application No. 61/154,218, filed on Feb. 20, 2009.

(51) Int. Cl.
*A61M 25/10* (2013.01)
(52) U.S. Cl.
USPC .......................................... 424/425; 424/424
(58) Field of Classification Search
USPC .................................. 424/422–426
See application file for complete search history.

(56) References Cited

U.S. PATENT DOCUMENTS

| 4,898,591 | A | 2/1990 | Jang et al. |
|---|---|---|---|
| 4,906,237 | A | 3/1990 | Johansson et al. |
| 5,290,585 | A | 3/1994 | Elton |
| 5,304,121 | A | 4/1994 | Sahatjian |
| 5,342,386 | A | 8/1994 | Trotta |
| 5,433,713 | A | 7/1995 | Trotta |
| 5,443,455 | A | 8/1995 | Hergenrother et al. |
| 5,525,348 | A | 6/1996 | Whitbourne et al. |
| 5,531,715 | A | 7/1996 | Engelson et al. |
| 5,576,072 | A | 11/1996 | Hostettler et al. |
| 5,585,057 | A | 12/1996 | Trotta |
| 5,603,991 | A * | 2/1997 | Kupiecki et al. ............. 427/508 |
| 5,662,960 | A | 9/1997 | Hostettler et al. |
| 5,693,034 | A | 12/1997 | Buscemi et al. |
| 5,750,206 | A | 5/1998 | Hergenrother et al. |
| 5,789,018 | A | 8/1998 | Engelson et al. |
| 5,919,570 | A | 7/1999 | Hostettler et al. |
| 6,017,577 | A | 1/2000 | Hostettler et al. |
| 6,030,656 | A | 2/2000 | Hostettler et al. |
| 6,040,058 | A | 3/2000 | Hostettler et al. |
| 6,080,488 | A | 6/2000 | Hostettler et al. |
| 6,221,061 | B1 | 4/2001 | Engelson et al. |
| 6,265,016 | B1 | 7/2001 | Hostettler et al. |
| 6,629,961 | B1 | 10/2003 | Israelsson et al. |
| 6,706,025 | B2 | 3/2004 | Engelson et al. |
| 7,348,055 | B2 | 3/2008 | Chappa et al. |
| 2002/0169472 | A1* | 11/2002 | Douk et al. .................. 606/200 |
| 2006/0030669 | A1 | 2/2006 | Taton et al. |
| 2006/0240072 | A1 | 10/2006 | Chudzik et al. |
| 2009/0041923 | A1 | 2/2009 | Lin et al. |

FOREIGN PATENT DOCUMENTS

WO    97/29160    8/1997

\* cited by examiner

*Primary Examiner* — Michael G Hartley
*Assistant Examiner* — Micah-Paul Young
(74) *Attorney, Agent, or Firm* — Vidas, Arrett & Steinkraus

(57) ABSTRACT

Articles such as catheters or balloons that have an ester-linked poly(ester-block-amide) substrate have a lubricious hydrogel coating which suppresses particle development under accelerated aging conditions. A polymerizable coating composition is applied to the substrate without application of an intervening primer layer and cured. The coating composition comprises an uncrosslinked polyvinylpyrrolidone polymer that is free of attached photoinitiator groups and at least one polyfunctional ethylenically unsaturated monomer.

11 Claims, No Drawings

HYDROPHILIC COATING THAT REDUCES PARTICLE DEVELOPMENT ON ESTER-LINKED POLY(ESTER-BLOCK-AMIDE)

CROSS-REFERENCE TO RELATED APPLICATIONS

This application claims the benefit of Application No. 61/154218, filed Feb. 20, 2009, the entire contents of which is hereby incorporated by reference.

BACKGROUND OF THE INVENTION

U.S. Pat. No. 4,898,591 describes catheter tubing formed of a blend of ester-linked PEBA (poly(ester-block-amide) with nylon 11. A lubricious hydrogel coating is applied to the surface. The lubricious coating may be a copolymer of polyurethane and polyvinylpyrrolidone or cross-linked copolymer of polyethylene oxide and polyhydroxyethyl methacrylate.

Surmodics, Inc. has described polymerizable compositions employing polyvinylpyrrolidone polymers that include photoinitiator groups thereon and use of such compositions on Pebax® polymer substrates in U.S. Pat. No. 7,348,055, US 2006/0030669 and US 20060240072. These compositions however are expensive to produce as the polymers with photoinitiator groups thereon must be specially prepared.

U.S. Pat. Nos. 5,585,057 and 5,433,713, Trotta, describe catheter tubing of ester-linked PEBA ("polyesteretheramides") such as Pebax® polymers have a blooming phenomena that is attributed to the ester linkage in these polymers. The blooming develops on accelerated aging and detrimentally affects adherence of hydrophilic coatings. These documents propose blending polyesteretheramide polymers having a Shore D hardness of greater than 70 with polyetheramides having no ester linkages, or with polyamides, to prevent particle blooming.

U.S. Pat. No. 6,629,961, Israelsson, also describes a blooming phenomena that occurs when ester-linked PEBA polymers (e.g. Pebax® polymers) are used for catheter tubing and teaches to use sequentially applied coatings of polyisocyanate and polyvinylpyrrolidone to avoid adherence problems despite the fact that blooming is sometimes observed after some months storage. This is attributed to the manner in which the coating is applied. The sequential coating provides a polyvinylpyrrolidone-polyurea interpolymer coating. The polyisocyanate coating step, however, substantially adds to the cost of this process.

U.S. Pat. No. 5,693,034 Busemi et al describes a lubricious coating for insertable medical devices such as catheters, balloons, and the like that is formed by polymerizing a polyfunctional acrylate monomer in a composition that also includes an uncrosslinked hydrogel polymer. Specific uncrosslinked hydrogel polymers that may be used include polyethylene oxide, polyacrylic acid, polyacrylamide, poly(sodium-4-styrenesulfonate), poly(3-hydroxybutyric acid), polyvinylpyrrolidone, and 2-hydroxyethyl methacrylate. One particular formulation according to U.S. Pat. No. 5,693,034 that has been commercialized is a lubricious coating in which the polyacrylate network is a polymer of neopentyl glycol diacrylate and the hydrogel polymer is polyethylene oxide. This coating has been successfully employed without significant problem on diverse substrates such as polyethylene, polyester, metals, polyester elastomers, and the like. The coating has the advantage that it involves a single application and that it can be photocured rapidly. However, when applied to substrates of Pebax® polymers that are susceptible to blooming, this polyethylene oxide/polyacrylate does not prevent particulate from passing therethrough. Under high humidity accelerated aging conditions high particle counts develop rapidly.

SUMMARY OF THE INVENTION

The present invention involves the surprising discovery that for a coating of the type described in U.S. Pat. No. 5,693,034 particle development on ester-linked poly(ether-block-amide) substrates is significantly suppressed, in a lubricious coating formed by polymerizing a polyfunctional acrylate monomer composition that also includes a hydrogel polymer, if the hydrogel polymer is polyvinylpyrrolidone instead of polyethylene oxide, even though the process does not include expensive additional primer coatings and the composition does not include expensive polymers with photoinitiator groups thereon.

In one aspect the invention is directed to an article having a substrate that is an ester-linked poly(ether-block-amide) polymer, the substrate is coated with a lubricious coating, and the coating is a polymerized composition, wherein the composition comprises at least one polyfunctional ethylenically unsaturated monomer and a polyvinylpyrrolidone polymer, and said polyvinylpyrrolidone polymer is free of photoinitiator groups thereon.

In another aspect the invention is directed to a method of suppressing development of surface particulates on an ester-linked poly(ether-block-amide) polymer substrate, the method comprising applying to the substrate a composition comprising at least one polyfunctional ethylenically unsaturated monomer and a polyvinylpyrrolidone polymer that has no photoinitiator groups thereon, and then polymerizing the at least one ethylenically unsaturated monomer to provide a cured coating on the substrate.

In some embodiments the substrate is medical catheter tubing and/or a medical balloon. In some embodiments the acrylate monomers are polymerized by irradiation. In some embodiments the composition is free of photoinitiator.

DETAILED DESCRIPTION OF THE INVENTION

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

The coated article of the present invention is formed by application of a polymerizable coating composition to an ester-linked poly(ether-block-amide) substrate and curing the composition. The polymerizable coating composition comprises an uncrosslinked polyvinylpyrrolidone polymer that is free of attached photoinitiator groups and at least one polyfunctional ethylenically unsaturated monomer. In some embodiments the substrate is activated, but in the present invention there is no need for separate application of a primer. Optionally the compositions may further contain a free radical initiator. The compositions are typically applied from a solvent which is evaporated before cure.

The polyfunctional ethylenically unsaturated monomers are compounds, including oligomeric compounds, that have a two or more ethylenically unsaturated groups thereon that may be readily polymerized by a radical mechanism to form a polymer. In some embodiments such compounds have a number average of about 5000 or less, for instance about 1000 or less. Suitable polyfunctional ethylenically unsaturated monomers include di and tri-functional (meth)acrylate esters, divinylbenzene and other divinyl monomers. Examples of polyfunctional ethylenically unsaturated monomers that may be used in the composition are neopentyl glycol diacrylate (NPG), ethylene glycol di(meth)acrylate, 1,3-propylene glycol di(meth)acrylate, 1,4-butanediol di(meth)acrylate, 1,6-hexanediol di(meth)acrylate, diethylene glycol di(meth)acrylate, triethylene glycol di(meth)acrylate, tetra ethylene glycol di(meth)acrylate, polyethylene glycol di(meth)acrylate, neopentyl glycol di(meth)acrylate, glyceryl propoxy triacrylate and alkoxylated trimethylol propane tri(meth)acrylates having about 2 to about 20 moles alkoxylate per molecule. In some embodiments the ethylenically unsaturated monomers that may be employed include alkoxylated, desirably ethoxylated or propoxylated, neopentyl glycol diacrylates, butanediol diacrylates, trimethylolpropane triacrylates, and glyceryl triacrylates for instance propoxylated trimethylol propane tri(meth)acrylate, ethoxylated pentaerythritol tetra(meth)acrylate, propoxylated neopentyl glycol diacrylate, propoxylated gylceryl tri(meth)acrylate, trimethylolpropane ethoxylate (1 EO/OH) methyl ether diacrylate, and so forth. In some embodiments an alkoxylated trimethylol propane triacrylate monomer is employed, suitably an ethoxylated trimethylol propane triacrylate. Such compounds are available from Sartomer Company, Inc. in Exton, Pa. Examples include SR 454 having 3 moles of ethoxylation, a molecular weight of 454 g/mole and a water solubility of 15 wt-% in water; SR 499 having 6 moles of ethoxylation and a molecular weight of 560 g/mole; SR 502 having 9 moles of ethoxylation and a molecular weight of 693 g/mole and SR9035 having 15 moles of ethoxylation and a molecular weight of 956 g/mole. Such compounds may also be found from Aldrich Chemical Co., Inc. in Milwaukee, Wis. having from 1 mole of alkoxylate and greater. Suitably, the alkoxylated (meth)acrylate compounds have some water solubility of about 15 wt-% or more, and even more desirably, about 50 wt-% or more.

Monofunctional ethylenically unsaturated monomers may also be included in the compositions. Examples include mono (meth)acrylate esters, styrene, acrylamide (meth)acrylamide and the like. In preferred embodiments functional ethylenically unsaturated monomers are present in minor amounts if at all, for instance 0-10 weight percent of the total weight of ethylenically unsaturated monomer in the composition.

The polyvinylpyrrolidone used in the polymerizable coating composition is a high molecular weight polymer free of photoactive species. Molecular weights in the range of at least 50,000 and above are most suitable, for instance about 100,000 or above, about 500,000 or above, or about 500,000-2 million (weight average MW). The polyvinylpyrrolidone also has not been grafted with photoinitiator groups. In particular embodiments the polyvinylpyrrolidone is a homopolymer having a molecular weight of at least 500,000. Examples of polyvinylpyrrolidone materials useful in this invention are those available from BASF Corp, Parsippany, N.J. as Kollidon 90, Luviskol K90, Luviskol K80 and Luviskol K60, and those available from GAF Corporation, as Plasdone 90, PVP K90 and PVP K120.

In some embodiments, a preferred weight ratio of polyvinylpyrrolidone to polyfunctional ethylenically unsaturated monomer(s) is in the range of from about 3:1 to about 12:1, or for instance about 4:1 to about 10:1.

Polymerization of the polymerizable coating composition may be facilitated by inclusion therein of a small amount of a non-polymeric free radical initiator in the coating composition. The non-polymeric free radical initiator may be a photoinitiator. Non-limiting examples of non-polymeric free radical photoinitiators that may be employed include benzophenones, ketones, acrylated amine synergists, α-amino ketones, benzil ketals, find utility herein. When a diacrylate is used, the mole ratio of free radical initiator to the ethylenically unsaturated monomer(s) is for instance about $10^4:1$. More specific examples of photoinitiators suitable for use herein include, but are not limited to, 2-phenyl-1-indanone; IRGACURE® 184 from Ciba Specialty Chemicals, BENACURE® 184 from Mayzo and SARCURE® SR1122 from Sartomer, all of which are 1-hydroxylcyclohexylphenyl ketone (HCPK); BENACURE® BP benzophenone; BENACURE® 651 and IRGACURE® 651, both of which are benzil dimethyl ketal or 2,2'dimethoxy-2-phenylacetophenone; BENACURE® 1732-hydroxy-2-methyl-1-phenyl-1-propanone; IRGACURE® 907 2-methyl 1-[4-methylthio)phenyl]2-morpholinopropan-1-one; IRGACURE® 369 morpholinoketone; and so forth and blends thereof. Photoinitiators are also available commercially in a variety of blends. Examples of commercially available blends include, but are not limited to, SARCURE® SR1136 is a blend of 4-methylbenzophenone and benzophenone; SARCURE® SR1137 is a blend of trimethylbenzophenone and methylbenzophenone; and BENACURE® 500, a blend of 1-hydroxyl-cyclohexylphenyl ketone and benzophenone.

In some embodiments of the invention the polymerizable composition has no free radical initiators.

Other optional additives may be employed in the polymerizable coating composition that do not materially affect the cure or blooming properties of the composition. Including, but not limited to, flow or viscosity modifiers, antioxidants, coupling agents, surfactants, and so forth. Any such components are included typically incorporated into the composition at levels less than 5%, more conventionally less than 2% based on the dry weight (i.e. excluding solvent) of the composition.

In preparing the coating composition for application to the substrate the polyvinylpyrrolidone is suitably mixed with ethylenically unsaturated monomer(s) in a solvent. Examples of suitable organic solvents include, but are not limited to, lower alcohols such as methanol, ethanol, and isopropyl alcohol (IPA); water; linear or cyclic carboxamides such ad N,N-dimethylacetamide (DMAC), N,N-diethylacetamide dimethylformamide (DMF), ethyl formamide, diethylformamide; N-methyl-2-pyrrolidone (NMP); dimethylsulphoxide (DMSO); acetonitrile; acetone and acetyl acetone; acrylonitrile; benzonitriledimethyl acetamide; 1,4-dioxane; dipropyl sulfone; aromatic solvents such as toluene and xylene; nitrobenzene; phenylacetate; propionitrile; and so forth. Preferred solvents are water soluble. Blends of solvents may be used, for instance water/IPA blends. In one preferred embodiment, isopropyl alcohol in combination with water acts as a suitable solvent.

The coating thickness will be affected by the ratio of solvent to coating composition and the technique of application. In some embodiments the coating thickness is desirably in the range of from 0.2 to 4 micrometers, for instance 0.5-2 micrometers. In some embodiments using a sponge coating application to catheter bodies coating thicknesses in this range can be provided at concentrations of coating composition in a solvent or solvent blend of about 2 to about 20% by weight, for instance 3-15% by weight or about 4-10%.

The mixture of solvent and coating composition may be applied to the medical device by any method known in the art including, but not limited to, spraying, dipping, painting, rolling, sponge painting, and so forth. The coating will then be allowed to dry, by evaporation of the solvent. The solvent may be more readily evaporated at an elevated temperature, although room temperature drying is acceptable.

According to the invention the substrate to which the coating composition is applied is an ester-linked PEBA polymer. The substrate may be for instance medical tubing such as catheter tubing or a medical balloon. For purposes of the present invention the substrate is defined as the surface material to which the coating is applied rather than bulk material thereunder. For instance, the ester-linked PEBA polymer substrate may be a surface layer of a multilayer tube or balloon whose under layer(s) is formed of another material. In some embodiments the ester-linked PEBA polymer has a Shore D hardness of from about 55 to about 75, for instance 55, 63, 70 or 72. Specific examples include Pebax® 5533, Pebax® 6333, Pebax® 7033, Pebax® 7233 and blends thereof.

No primer layer or coupling agent is applied to the substrate before the coating is applied. However, in some embodiments, the substrate may be treated with plasma or corona discharge before application of the coating composition.

Once a coating has been applied to a substrate, the coating is cured by exposing the coating to heat or actinic radiation such as UV light for a short period of time. This initiates polymerization crosslinking of the ethylenically unsaturated monomer(s). The polyfunctionality of at least some of the ethylenically unsaturated monomer(s) produces a high degree of crosslinking upon polymerization. At least for compositions based on acrylate esters it is generally desirable to cure in a low oxygen atmosphere, such as under a blanket of nitrogen, helium or argon gas. The amount of time needed to cure the surface is dependent on the source of energy, the relative amounts of constituents in the composition, the thickness of the coating desired, and other factors. Generally, the amount of time required for thermal cure is from about 1 to 30 minutes. UV curing requires less time and can generally be in the range of about two minutes or less. Curing around and along the substrate can be accomplished by incrementally or continuously using irradiation from multiple angles using spaced lamps and/or reflectors; rotation of the substrate, light source a light beam; longitudinal movement of the substrate, light source or light beam; or a combination of such techniques.

The polymerizable composition is typically cured by irradiation with a suitable source of activating radiation such as ultraviolet (UV), X-ray or e-beam radiation. Light sources may be narrow or broad spectrum or laser beam sources. Suitably the mixture is cured using a high intensity broad spectrum ultraviolet lamp such as mercury arc capillary lamps which have some output in the UVC region (280 nm-100 nm). In some embodiments the composition is photocured with UV lamps that are sequenced or pulsed in a way that allows for some heat dissipation during the curing cycle.

While the polyvinylpyrrolidone polymer has no photoactive groups thereon, the cure conditions employed may provide some crosslinking between the polyvinylpyrrolidone polymer and the polymer produced by curing the ethylenically unsaturated monomer(s), for instance if a hydrogen atom is abstracted from the polymer by the UV irradiation or the polymer becomes involved in termination or chain transfer reactions. In some embodiments a particular advantage of the composition is that after cure the polyvinylpyrrolidone component is substantially unextractable by water and IPA.

The cured coating has a high durability after extended aging at elevated temperature and high humidity conditions and significantly impedes development of surface particulate derived from the underlying ester-linked PEBA substrate.

In some embodiments the coating may be useful as a drug delivery system. By varying such parameters as PVP molecular weight and functionality of the ethylenically unsaturated monomer, a coating composition can be formulated that allows a drug to be incorporated into the polymer network of the cured coating. The drug may be added to the coating composition prior to curing or absorbed into the coating after it has cured. The drug is carried in the polymer network and leaches out of the coating when the coating is wet, delivering the drug to immediately adjacent areas of the body.

The invention is illustrated by the following non-limiting examples.

EXAMPLES

Raw Materials:
Polyvinyl pyrrolidone (PVP), Mol. Weight. 1,300,000, Aldrich, # 43719-0
Neopentyl glycol diacrylate (NPG),
2-Propanol (IPA), HPLC 99.5%
RO water
Over-the-wire catheters manufactured by Boston Scientific Corporation that had a distal shaft of Pebax® 7033 were employed in these Examples. These catheters were exposed to helium plasma in a commercial treatment system prior to coating. The coatings were applied and cured within 24 hours of plasma treatment.

Coating Compositions:
A solvent mixture of water and IPA was prepared at 1 to 3 weight basis water to IPA. Polyvinylpyrrolidone, 10 parts by weight, was then dissolved in 90 parts by weight solvent ("10% PVP solution"). A coating composition was then prepared by adding 1 part by weight neopentyl glycol diacrylate to 50 parts by weight of the 10% PVP solution. The composition was designated "W/IPA 1/3."

Another coating composition was prepared in the same manner except that the solvent mixture was 1 to 6, weight ratio of water to IPA. This additional composition was designated "W/IPA 1/6."

For comparison a commercial UV curable coating composition designated "PEO/acrylate," having approximately 2% solids and containing polyethylene glycol, and neopentyl glycol diacrylate in a weight ratio of about 10:1, in a water/IPA solvent mixture (1:4 weight ratio). Azobisisonitrile was present in the PEO/acrylate composition in an amount of about 0.008% by weight relative to the NPG.

Application and Cure:
Catheters were coated along the outer shaft up to the balloon using a sponge wipe coater with the solvent mixture of the respective coating compositions.

Coated catheters were mounted in spaced straight parallel arrangement in fixtures that were then placed in a UV curing oven and subjected to a curing protocol that applied UV energy to the surface of the catheters from multiple angles so that the coating was cured around the circumference of the tubing. Integrated UV energy intensity was measured at several points near the surface of the catheters. For the W/IPA 1/3 sample, the UV lamps were alternatingly turned on an off during curing. The typical dosage taken as the average measured intensity multiplied by the irradiation time.

Testing:
Catheters from each cure protocol were selected for initial (t=0) lubricity and durability (L&D) testing. A catheter was cut into equal length pieces, the pieces submerged in water, weighed down with an 80 gram weight and subjected to reciprocal pulling and pushing cycle, measuring the frictional force (in grams) required to move the catheter piece initially (t=0) and through successive cycles. Both distal and proximal sections of the selected catheters were tested. The coating thickness was determined on a central portion of the catheters. Average coating thickness for the PEO/acrylate coating was about 0.2 micrometer. Average coating thickness for the coatings of the invention were in the range of about 1.2-2 micrometers due to the higher solids concentration and viscosity.

Three additional catheters were used for measurement of surface particulate count at t=0. The catheters were inserted in a tubluar test apparatus with bends constructed to simulate features of clinical deployment. Water was circulated over the catheters for a fixed period of time. Particles larger than 10 micrometer that were transferred into the circulating water were counted using a laser particle counter.

Other catheters from each batch were placed into an accelerated aging oven at 40° C. and 75% RH.

After 90 days in the accelerated aging oven (t=90) catheters from each batch were removed and tested for lubricity and durability or for particle count as described above.

Several catheters from each batch were left in the accelerated aging oven for 180 days (T=180), after which they were removed and subjected to six additional catheters from each batch were removed from the aging oven. Three were tested for L&D and three for particulate count at t=180. These conditions are considered roughly equivalent to 18 months aging at typical room temperature and humidity.

Table 1 gives the average values for the tested properties of the catheter coatings at 0, 90 and 180 days. As can be seen from the data the invention examples are much superior in Lubricity, Durability and particle count.

TABLE 1

| Coating | PEO/Acrylate Comparative | INVENTION W/IPA 1/3 | INVENTION W/IPA 1/6 |
|---|---|---|---|
| Typical | | | |
| UVC Dose L&D T = 0 | 0.12 J/cm$^2$ | 0.04 J/cm$^2$ | 0.12 J/cm$^2$ |
| Cycle 2, | 5.6 g | 2.2 g | 2.8 g |
| Cycle 20 | 6.6 g | 3.4 g | 2.8 g |
| Particle count | | | |
| T = 0, (>10 μm) L&D T = 90 | 1000 | 1500 | 1600 |
| Cycle 2, | 33.9 g | 2.7 g | 3.3 g |
| Cycle 20 | 44.5 g | 2.6 g | 3.0 g |
| Particle count | | | |
| T = 90, (>10 μm) L&D T = 180 | 8200 | 900 | 1400 |
| Cycle 2, | 26.3 g | 2.5 g | 2.7 g |
| Cycle 20 | 37.0 g | 2.6 g | 2.3 g |
| Cycle 100 | — | 2.5 g | 2.3 g |
| Particle count | | | |
| T = 180, (>10 μm) | 63,000 | 1100 | 700 |

The above examples and disclosure are intended to be illustrative and not exhaustive. These examples and description will suggest many variations and alternatives to one of ordinary skill in this art. All these alternatives and variations are intended to be included within the scope of the claims, where the term "comprising" means "including, but not limited to". Those familiar with the art may recognize other equivalents to the specific embodiments described herein which equivalents are also intended to be encompassed by the claims. Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all claims which possess all antecedents referenced in such dependent claim if such multiple dependent format is an accepted format within the jurisdiction. In jurisdictions where multiple dependent claim formats are restricted, the following dependent claims should each be also taken as alternatively written in each singly dependent claim format which creates a dependency from an antecedent-possessing claim other than the specific claim listed in such dependent claim.

The invention claimed is:

1. A method of suppressing development of surface particulates on an ester-linked poly(ether-block-amide) polymer substrate, the method comprising applying to the substrate a composition comprising at least one polyfunctional ethylenically unsaturated monomer and a polyvinylpyrrolidone polymer that has no photoinitiator groups thereon and then polymerizing the at least one polyfunctional ethylenically unsaturated monomer to provide a cured coating on the substrate.

2. The method as in claim 1 wherein the substrate is treated with a plasma or corona discharge before application of said composition to the substrate.

3. A method as in claim 1 wherein the composition is photocured on the substrate.

4. A method as in claim 1 wherein said at least one polyfunctional ethylenically unsaturated monomer is a polyfunctional acrylate monomer or blend thereof 5. A method as in claim 1 wherein said composition is applied from a mixture with solvent, and the solvent is evaporated before polymerization of the at least one polyfunctional ethylenically unsaturated monomer.

6. A method as in claim 5 wherein the concentration of said composition in said solvent mixture is from about 2 to about 20% by weight.

7. A method as in claim 1 wherein said wherein said substrate is surface of a medical catheter or balloon.

8. The method as in claim 1 wherein the substrate is treated with a plasma or corona discharge before application of said composition to the substrate and the composition is photocured on the substrate.

9. A method as in claim 8 wherein said at least one polyfunctional ethylenically unsaturated monomer is a polyfunctional acrylate monomer or blend thereof.

10. A method as in claim 8 wherein said wherein said substrate is surface of a medical catheter or balloon.

11. A method as in claim 5 wherein said wherein said substrate is surface of a medical catheter or balloon.

* * * * *

UNITED STATES PATENT AND TRADEMARK OFFICE
CERTIFICATE OF CORRECTION

PATENT NO. : 8,617,586 B2
APPLICATION NO. : 12/704390
DATED : December 31, 2013
INVENTOR(S) : Irina Nazarova, Jeffrey S. Lindquist and Daniel Horn Page 1 of 1

It is certified that error appears in the above-identified patent and that said Letters Patent is hereby corrected as shown below:

In the Claims

Claim 7, at column 8, line 50, the text "wherein said wherein said" should be replaced by the text --wherein said--.

Claim 10, at column 8, line 59, the text "wherein said wherein said" should be replaced by the text --wherein said--.

Claim 11, at column 8, line 61, the text "wherein said wherein said" should be replaced by the text --wherein said--.

Signed and Sealed this
Fifteenth Day of April, 2014

Michelle K. Lee
*Deputy Director of the United States Patent and Trademark Office*